(12) United States Patent
Gordon, III et al.

(10) Patent No.: US 8,054,939 B2
(45) Date of Patent: Nov. 8, 2011

(54) TANGENT RADIOGRAPHY USING BRILLIANT X-RAY SOURCE

(75) Inventors: Clarence Lavere Gordon, III, Renton, WA (US); Richard H. Bossi, Renton, WA (US); John L. Adamski, Kenmore, WA (US)

(73) Assignee: The Boeing Company, Chicago, IL (US)

( * ) Notice: Subject to any disclaimer, the term of this patent is extended or adjusted under 35 U.S.C. 154(b) by 217 days.

(21) Appl. No.: 12/512,184

(22) Filed: Jul. 30, 2009

(65) Prior Publication Data
US 2011/0026675 A1  Feb. 3, 2011

(51) Int. Cl.
*G01B 15/06* (2006.01)

(52) U.S. Cl. .............................. 378/58; 378/59

(58) Field of Classification Search ............ 378/57, 378/58, 59, 119
See application file for complete search history.

(56) References Cited

U.S. PATENT DOCUMENTS

| | | | |
|---|---|---|---|
| 2,735,018 A * | 2/1956 | McLachlan | 378/43 |
| 3,766,387 A * | 10/1973 | Heffan et al. | 378/58 |
| 5,042,055 A | 8/1991 | Wirt et al. | |
| 5,577,091 A * | 11/1996 | Richardson et al. | 378/119 |
| 5,754,621 A * | 5/1998 | Suzuki et al. | 378/57 |
| 5,870,450 A | 2/1999 | Khutoryansky et al. | |
| 6,229,872 B1 | 5/2001 | Amos | |
| 6,256,372 B1 | 7/2001 | Aufrichtig et al. | |
| 6,333,966 B1 | 12/2001 | Schoen | |
| 6,678,350 B2 | 1/2004 | Dolazza et al. | |
| 6,873,677 B2 | 3/2005 | Kaufman | |
| 7,031,429 B2 | 4/2006 | Akagi | |
| 7,127,090 B2 | 10/2006 | Kreang-Arekul et al. | |
| 7,187,753 B2 | 3/2007 | Freudenberger et al. | |
| 7,236,564 B2 | 6/2007 | Hopkins et al. | |
| 7,280,636 B2 | 10/2007 | Morrison et al. | |
| 7,310,408 B2 | 12/2007 | Filkins et al. | |
| 7,321,604 B2 | 1/2008 | Umstadter et al. | |
| 7,356,115 B2 | 4/2008 | Ford et al. | |
| 7,412,025 B1 | 8/2008 | Bossi et al. | |
| 7,522,755 B2 | 4/2009 | Li et al. | |

(Continued)

FOREIGN PATENT DOCUMENTS

EP  0802705 A2  10/1997
(Continued)

OTHER PUBLICATIONS

USPTO office action for U.S. Appl. No. 12/154,214 dated Dec. 28, 2009.
(Continued)

*Primary Examiner* — Glen Kao
(74) *Attorney, Agent, or Firm* — Yee & Associates, P.C.

(57) ABSTRACT

A method and apparatus for measuring a structure. An x-ray system and the structure are positioned relative to each other. The x-ray system comprises a gas source configured to provide a gas, a laser system configured to emit a laser beam, a steering system, and a detector. The steering system is configured to direct a first portion of the laser beam into the gas such that an electron beam is generated by the laser beam interacting with the gas and is configured to direct a second portion of the laser beam into the electron beam such that a collimated x-ray beam is formed. The detector is configured to detect the collimated x-ray beam. The collimated x-ray beam is emitted with the structure positioned relative to the x-ray system.

19 Claims, 6 Drawing Sheets

U.S. PATENT DOCUMENTS

| | | | |
|---|---|---|---|
| 2002/0057760 A1 | 5/2002 | Carroll et al. | |
| 2002/0094062 A1 | 7/2002 | Dolazza et al. | |
| 2003/0026469 A1 | 2/2003 | Kreang-Arekul et al. | |
| 2004/0109532 A1 | 6/2004 | Ford et al. | |
| 2004/0208276 A1 | 10/2004 | Kaufman | |
| 2004/0213372 A1 | 10/2004 | Akagi | |
| 2004/0218718 A1 | 11/2004 | Freudenberger et al. | |
| 2004/0240506 A1* | 12/2004 | Sandstrom et al. | 372/55 |
| 2005/0069086 A1* | 3/2005 | Deych et al. | 378/112 |
| 2005/0117705 A1 | 6/2005 | Morrison et al. | |
| 2005/0147147 A1* | 7/2005 | Umstadter et al. | 372/73 |
| 2006/0204076 A1 | 9/2006 | Avinash et al. | |
| 2007/0034805 A1 | 2/2007 | Hopkins et al. | |
| 2010/0072405 A1* | 3/2010 | Yu et al. | 250/493.1 |
| 2010/0290587 A1* | 11/2010 | Umstadter et al. | 378/57 |

FOREIGN PATENT DOCUMENTS

| | | |
|---|---|---|
| JP | 2002323598 A | 11/2002 |
| WO | 2005069451 A1 | 7/2005 |
| WO | 2006104956 A2 | 10/2006 |

OTHER PUBLICATIONS

USPTO office action for U.S. Appl. No. 12/259,753 dated Feb. 4, 2010.

Dilmanian, "Computed Tomography with Monochromatic Xrays", American Journal of Physiological Imaging, 1992: 7 (3-4) 175-93.

USPTO final office action for U.S. Appl. No. 12/145,214 dated Mar. 26, 2010.

Coumans, "Duel-energy X-ray Diagnostics," Philips Tech. Rev. 42, No. 8/9 pp. 274-285, Jun. 24, 1986.

Lehmann et al., "Generalized Image Combination in Dual kVp Digital Radiography," Med. Phys. 8 (5), Sep./Oct. 1981, pp. 659-666.

Engler et al., "Review of Duel-Energy Computed Tomography Techniques," The American Society for Nondestructive Testing, Inc., Materials Evaluation, 48 May 1990, pp. 623-629.

Dobashi et al., "Development of Compact Hard X-ray Source Based on Laser-Electron Collision Using X-Band Linac", Proceedings of EPAC 2002, Paris France, pp. 677-679, (2002).

Carroll, "Tunable, Monochromatic X-Rays: An Enabling Technology for Molecular/Cellular Imaging and Therapy", Journal of Cellular Biochemistry, 2003, pp. 90: 502-508.

Schwartz, "Use of Tangential Radiography and Resonance Ultrasonic Techniques to Evaluate Bonding Quality", pp. 1-7, retrieved Jul. 21, 2009. http://www.ndt.net/article/wcndt2004/pdf/materials_characterization/304_schwartz.pdf.

Tritz et al., "Tangential soft x-ray imaging for shape and current profile measurements", Review of Scientific Instruments, vol. 74, No. 3, Mar. 2003, pp. 2161-2164.

Rousse et al., "Production of a keV X-Ray Beam from Synchrotron Radiation in Relativistic Laser-Plasma Interaction", The American Physical Society, vol. 93, No. 13, Sep. 2004, pp. 135005-1 to 135005-4.

Burkle, "Application of the Tangential Radiographic Technique for Evaluating Pipe System Erosion/Corrosion", Materials Evaluation/47/Oct. 1989, The American Society for Nondestructive Testing, Inc., pp. 1184-1188.

Burkle et al., "Burnoff and Film Latitude in the Tangential Radiographic Technique", Materials Evaluation/Nov. 1992, The American Society for Nondestructive Testing, Inc., pp. 1274-1277.

Viswanathan et al., "Performance Characteristics of Conventional X-Ray Generator, Isotope Source, and High-Energy Accelerator in Rocket Motor Evaluation", Materials Evaluation, Jan./Feb. 1987, American Society for Nondestructive Testing, Inc., pp. 86-90.

"Standard Guide for Radioscopy", ASTM International Designation: E1000-98 (Reapproved 2009), pp. 1-31, (2009).

Leemans et al., "GeV electron beams from a centimetre-scale accelerator", nature physics, vol. 2, Oct. 2006, pp. 696-699.

U.S. Appl. No. 12/259,753, filed Oct. 28, 2008, Gordon, III et al.

U.S. Appl. No. 12/145,214, filed Jun. 24, 2008, Parazzoli et al.

GB Search and Examination Report for application GB1012901.3 dated Oct. 12, 2010.

* cited by examiner

| PERFORMANCE CRITERIA | LINEAR ACCELERATOR | LASER WAKEFIELD ACCELERATOR |
|---|---|---|
| FOCAL SPOT SIZE | 2 MM | 0.1 MM |
| IMAGE UNSHARPNESS (4X MAGNIFICATION) | 6 MM | 0.3 MM |
| AVERAGE ENERGY | 1 MeV | 5-25 MeV |
| ELECTRON BEAM ENERGY | 9 MeV | 400 MeV - 1GeV |
| CONE ANGLE (DEGREES) | 20 | <1 |
| FLUX FALLOFF vs. DISTANCE | $1/R^2$ | $<1/R^2$ |

TANGENT RADIOGRAPHY USING BRILLIANT X-RAY SOURCE

BACKGROUND INFORMATION

1. Field

The present disclosure relates generally to measuring structures and, in particular, to measuring edges of structures. Still more particularly, the present disclosure relates to a method and apparatus for measuring the edge of cylindrical structures using x-rays.

2. Background

Radiography uses x-rays to view unseen or hard-to-image objects. Radiography has both medical and industrial applications. With respect to industrial applications, x-rays are used to make measurements. In particular, the measurement made from x-rays may be used as one form of non-destructive testing. X-rays are used to inspect materials for inconsistencies using x-rays to penetrate various materials. X-rays also are used to test and grade welds on objects. These objects include, for example, pressurized piping, pressure vessels, high-capacity storage containers, pipes, structural welds, machine parts, metal plates, and/or other suitable objects.

One type of radiography is tangent radiography. For example, tangent radiography is commonly used to make measurements of pipe walls. These measurements may be used to identify pipe wall thinning. Further, tangent radiography also has been used to look for bond separation and check liner conditions. Tangent radiography is commonly used to detect fine detail in the edges of cylindrical or curved structures. Tangent radiography is used to check for gaps, fit up, corrosion, degradation, and/or other types of inconsistencies.

For example, currently available tangent radiography systems may be used to make measurements of large structures, such as those greater than two meters in diameter. This type of radiography, however, has limitations in usefulness as the structure increases in size to around 10 meters or more in diameter. The standoff distances and trade-off in resolution and sensitivity make a quantitative evaluation of some structures impractical.

As a result, this type of measurement is rarely applied to aircraft. With rockets and missile systems, this type of radiography may be used with limitations to the resolution and the size of features that can be measured or detected. With tangential radiography, the x-ray beam unsharpness decreases the resolution and the size of features that can be measured or detected.

One solution may involve moving the detector closer to the region of interest. With a cylinder, the detector may be moved to take into account the change in transmission length at the edge of the cylinder. However, limitations may be present on how close the detector can be placed with respect to the location containing a feature.

The energies used to obtain the desired results may add to the scattering and size of the radiation fields that occur for this type of measurement. As a result, extensive shielding or having operators located remotely from the testing site may be required. These types of limitations increase the expense and/or decrease the feasibility of performing tests using tangential radiography for structures, such as aircraft.

Therefore, it would be advantageous to have a method and apparatus that takes into account one or more of the issues discussed above, as well as possibly other issues.

SUMMARY

In one advantageous embodiment, a method is present for sending x-rays through a structure. An x-ray system and the structure are positioned relative to each other. The x-ray system comprises a gas source configured to provide a gas, a laser system configured to emit a laser beam, a steering system, and a detector. The steering system is configured to direct a first portion of the laser beam into the gas such that an electron beam is generated by the laser beam interacting with the gas and is configured to direct a second portion of the laser beam into the electron beam such that a collimated x-ray beam is formed. The detector is configured to detect the collimated x-ray beam. The collimated x-ray beam is emitted with the structure positioned relative to the x-ray system.

In another advantageous embodiment, a method is present for sending x-rays through a structure. An x-ray source and a detector are positioned relative to a feature in a location on the structure. The x-ray source emits a collimated x-ray beam at a substantially single energy level. The substantially single energy level is selected to allow the collimated x-ray beam to penetrate the structure. The x-ray source has a focal spot having a size selected for a desired magnification, a desired x-ray flux level, and a desired level of unsharpness. The collimated x-ray beam is emitted from the x-ray source and the detector positioned relative to the feature in the location on the structure.

In another advantageous embodiment, an apparatus comprises a gas source configured to provide a gas, a laser system configured to emit a laser beam, a steering system, and a detector. The steering system is configured to direct a first portion of the laser beam into the gas such that an electron beam is generated by the laser beam interacting with the gas and is configured to direct a second portion of the laser beam into the electron beam such that a collimated x-ray beam is formed. The detector is configured to detect the collimated x-ray beam.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the advantageous embodiments are set forth in the appended claims. The advantageous embodiments, however, as well as a preferred mode of use, further objectives, and advantages thereof, will best be understood by reference to the following detailed description of an advantageous embodiment of the present disclosure when read in conjunction with the accompanying drawings, wherein:

DETAILED DESCRIPTION

Figure 1:
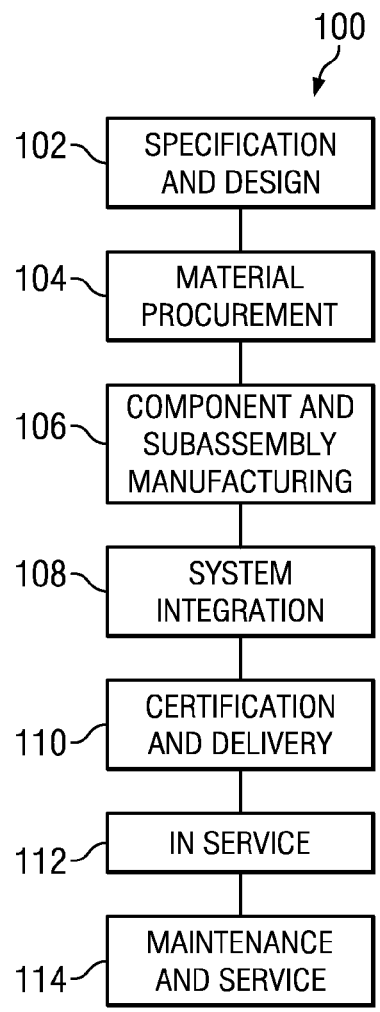
FIG. 1 is an illustration of an aircraft manufacturing and service method in accordance with an advantageous embodiment.
Figure 2:
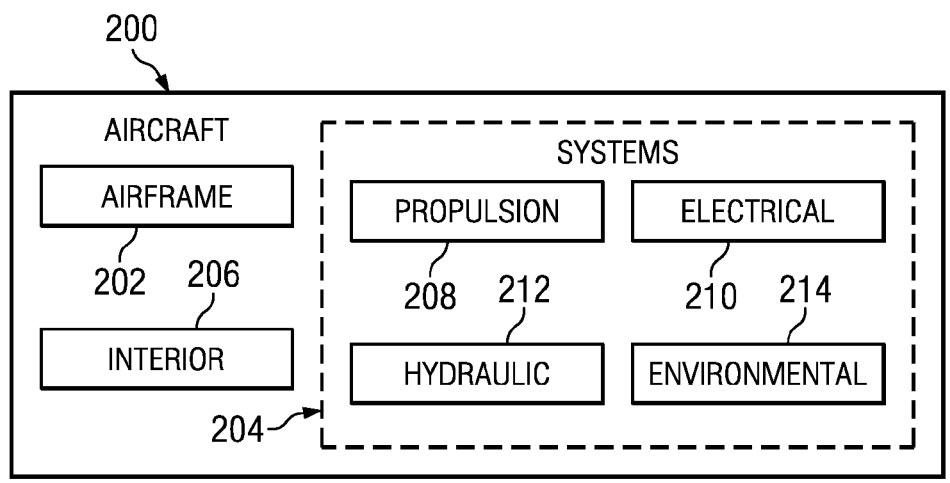
FIG. 2 is an illustration of an aircraft in which an advantageous embodiment may be implemented.

Referring more particularly to the drawings, embodiments of the disclosure may be described in the context of aircraft manufacturing and service method 100 as shown in FIG. 1 and aircraft 200 as shown in FIG. 2. Turning first to FIG. 1, an illustration of an aircraft manufacturing and service method is depicted in accordance with an advantageous embodiment. During pre-production, aircraft manufacturing and service method 100 may include specification and design 102 of aircraft 200 in FIG. 2 and material procurement 104.

During production, component and subassembly manufacturing 106 and system integration 108 of aircraft 200 in FIG. 2 takes place. Thereafter, aircraft 200 in FIG. 2 may go through certification and delivery 110 in order to be placed in service 112. While in service by a customer, aircraft 200 in FIG. 2 is scheduled for routine maintenance and service 114, which may include modification, reconfiguration, refurbishment, and other maintenance or service.

Each of the processes of aircraft manufacturing and service method 100 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of venders, subcontractors, and suppliers; and an operator may be an airline, leasing company, military entity, service organization, and so on.

With reference now to FIG. 2, an illustration of an aircraft is depicted in which an advantageous embodiment may be implemented. In this example, aircraft 200 is produced by aircraft manufacturing and service method 100 in FIG. 1 and may include airframe 202 with a plurality of systems 204 and interior 206. Examples of systems 204 include one or more of propulsion system 208, electrical system 210, hydraulic system 212, and environmental system 214. Any number of other systems may be included. Although an aerospace example is shown, different advantageous embodiments may be applied to other industries, such as the automotive industry.

Apparatus and methods embodied herein may be employed during at least one of the stages of aircraft manufacturing and service method 100 in FIG. 1 to make measurements of aircraft 200 and parts or substructures for aircraft 200. These measurements may be used as part of nondestructive testing of aircraft 200 and parts or substructures for aircraft 200. As used herein, the phrase "at least one of", when used with a list of items, means that different combinations of one or more of the listed items may be used and only one of each item in the list may be needed. For example, "at least one of item A, item B, and item C" may include, for example, without limitation, item A or item A and item B. This example also may include item A, item B, and item C or item B and item C.

In one illustrative example, measurements of subassemblies produced in component and subassembly manufacturing 106 in FIG. 1 may be made in a manner similar to measurements for components or subassemblies produced while aircraft 200 is in service 112 in FIG. 1. As yet another example, a number of apparatus embodiments, method embodiments, or a combination thereof may be utilized during production stages, such as component and subassembly manufacturing 106 and system integration 108 in FIG. 1. A number, when referring to items, means one or more items. For example, a number of apparatus embodiments is one or more apparatus embodiments. A number of apparatus embodiments, method embodiments, or a combination thereof may be utilized while aircraft 200 is in service 112 and/or during maintenance and service 114 in FIG. 1. The use of a number of the different advantageous embodiments may substantially expedite the assembly of and/or reduce the cost of aircraft 200.

The different advantageous embodiments recognize and take into account a number of different considerations. For example, currently available conventional x-ray sources may be impractical for use in making measurements for large structures and, in particular, large cylindrical structures. Examples of large structures may include an aircraft, a rocket motor, a missile, and/or some other suitable structure.

The different advantageous embodiments recognize that the energy level for an x-ray beam that allows the x-ray beam to penetrate a structure varies with the thickness of the structure at the location at which the x-ray beam is aligned. For example, as the thickness of the structure increases, the x-ray beam energy level required to penetrate the thickness of the structure also increases. Further, the capability of an x-ray system to detect and/or make measurements for features of interest varies with the energy level of an x-ray beam. In other words, when the energy level for an x-ray beam increases, the ability of an x-ray system to detect and/or make measurements for particular features of interest may be reduced.

For structures of substantially the same size, an x-ray beam of a higher energy level is used to send the x-ray beam through a solid or near-solid structure as compared to the energy level needed for a shell-type structure. A rocket motor may be one example of a solid or near-solid structure. The fuselage of an aircraft may be one example of a shell-type structure. A fuselage has a shell layer with a hollow or near-hollow inner region.

Further, the different advantageous embodiments also take into account and recognize that imaging large structures may require positioning the detector at a distance from the structure greater than desired when using conventional x-ray sources. The different advantageous embodiments recognize that as the distance between a detector and a structure is increased, the geometrical unsharpness is reduced. The geometrical unsharpness is a quantitative measure relating to the level of detail that may be detected for a structure. In other words, with a higher reduced geometrical unsharpness, or higher spatial resolution, features of a certain size may be detected.

The different advantageous embodiments also recognize and take into account that imaging of structures with conventional x-ray sources may require access to the inside of the structure. The access may be limited or prohibited in some cases. The different advantageous embodiments recognize that image resolution may be reduced if internal access to the structure is unavailable.

The different advantageous embodiments recognize and take into account that measurements may be made more accurately when using a collimated x-ray beam with a focal spot having a size selected to reduce and/or minimize geometrical unsharpness. The selected size for the focal spot also may provide x-ray flux at a desired level when using magnification to make measurements.

X-ray flux is the total number of photons per unit of time that travel through a specified aperture in these examples. X-ray flux decreases as the distance between the x-ray source and the detector increases. Further, with a desired size for a focal spot, a collimated x-ray beam can be generated having higher energy levels as compared to currently available x-ray sources. The higher energy levels allow for increased penetration in structures as compared to currently used systems. Further, with a collimated x-ray beam, the exposure of other locations outside the location containing the features of interest may be reduced.

Thus, the different advantageous embodiments provide a method and apparatus for sending x-rays though a structure. In one advantageous embodiment, an apparatus comprises a gas source, a laser system, a steering system, and a detector. The gas source is configured to provide a gas. The laser system is configured to emit a laser beam. The steering system is configured to direct a first portion of the laser beam into the gas such that an electron beam is generated by the laser beam interacting with the gas. Further, the steering system is configured to direct a second portion of the laser beam into electron beams such that a collimated x-ray beam is formed. The detector is configured to detect the collimated x-ray beam.

In these illustrative examples, an x-ray system and the structure are positioned relative to each other. The collimated x-ray beam is emitted with the structure positioned relative to the x-ray system. Information may be obtained from the detector for making measurements and/or performing an analysis of a feature on the structure.

Figure 3:
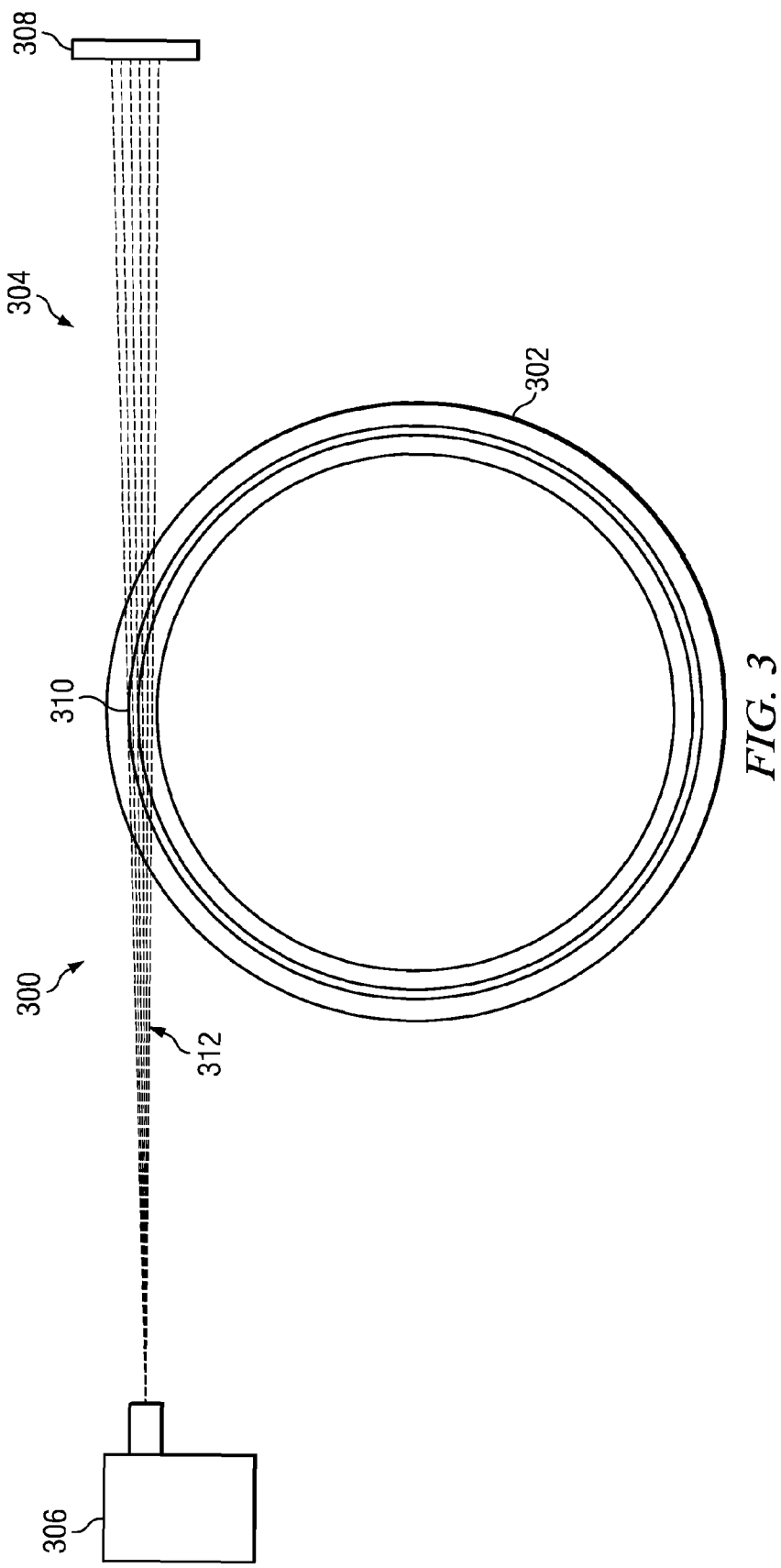
FIG. 3 is an illustration of a configuration of components for performing tangent radiography in accordance with an advantageous embodiment.

Turning now to FIG. 3, an illustration of a configuration of components for performing tangent radiography is depicted in accordance with an advantageous embodiment. In this illustrative example, configuration 300 is an example of a configuration of components that may be used to obtain information about structures using x-ray beams. In this illustrative example, configuration 300 is an example of a setup that may be used to make measurements of structure 302. Structure 302 may be, for example, without limitation, aircraft 200 in FIG. 2.

In this example, x-ray system 304 includes x-ray source 306 and detector 308. X-ray source 306 and detector 308 are positioned relative to structure 302.

In this illustrative example, feature 310 is a feature of interest for which measurements are to be made. In this illustrative example, feature 310 may be, for example, without limitation, an angular feature, a fit up, a gap, or another suitable feature.

X-ray source 306 emits x-ray beam 312, such that x-ray beam 312 passes through feature 310 in a manner that is substantially tangent to structure 302. X-ray beam 312 is then detected by detector 308. The information from detector 308 is used to obtain measurements for feature 310 on structure 302. These measurements may be used for a number of different purposes. For example, the measurements may be used to determine whether a gap has a correct width, whether corrosion is present, and/or whether other inconsistencies may be present in feature 310.

In the different advantageous embodiments, x-ray source 306 is configured to provide a focal spot size that may result in a higher level of x-ray flux levels as compared to currently used x-ray sources. Further, x-ray beam 312 takes the form of a directional collimated beam. In this manner, the amount of x-rays outside of the region of interest in structure 302 may be reduced as compared to currently used x-ray systems.

Further, x-ray source 306 emits x-ray beam 312 at an energy level selected to allow x-ray beam 312 to penetrate structure 302 and reach detector 308. This energy level may be, for example, without limitation, an energy level equal to or greater than around one megavolt.

Still further, x-ray source 306 may emit x-ray beam 312 at a substantially single energy level. Different portions of an x-ray beam may have different energy levels even when the x-ray beam is a collimated x-ray beam or a substantially collimated x-ray beam. In these illustrative examples, x-ray source 306 may emit x-ray beam 312 such that substantially all portions of x-ray beam 312 are at a substantially single energy level. In these illustrative examples, x-ray system 304 may be a portable system.

Figure 4:
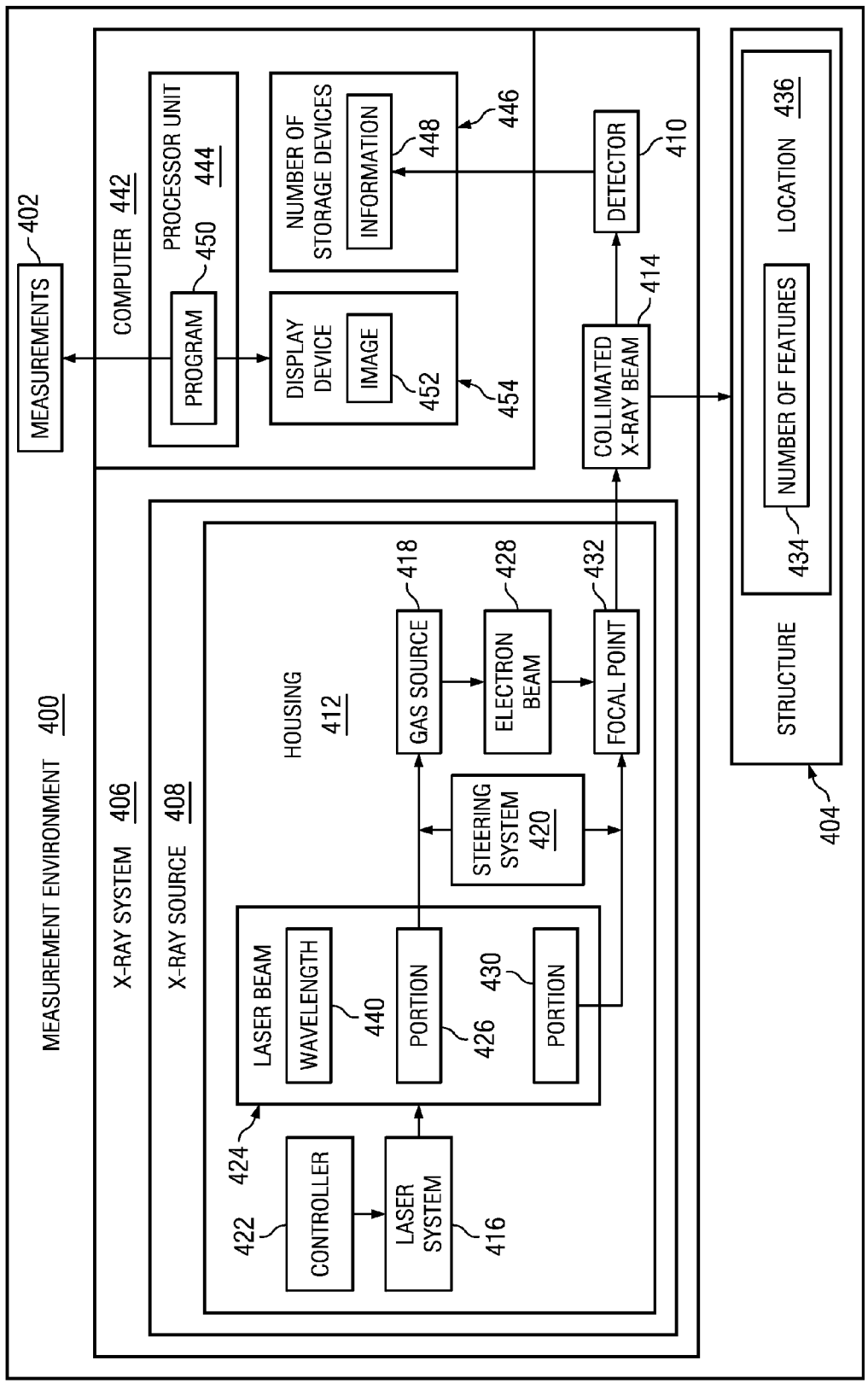
FIG. 4 is an illustration of a measurement environment in accordance with an advantageous embodiment.

With reference now to FIG. 4, an illustration of a measurement environment is depicted in accordance with an advantageous embodiment. In this illustrative example, measurement environment 400 is an example of an environment that may be used to perform measurements of structures, such as aircraft 200 in FIG. 2. In this illustrative example, measurement environment 400 may include a configuration, such as configuration 300 in FIG. 3.

Measurement environment 400 is used to make measurements 402 of structure 404 with x-ray system 406. X-ray system 406, in this example, includes x-ray source 408 and detector 410. X-ray source 408 includes housing 412. Laser system 416, gas source 418, steering system 420, and controller 422 are located in housing 412 and are part of x-ray source 408 in these illustrative examples.

Housing 412 takes the form of a portable housing. In other words, housing 412 may be moved relative to structure 404. In one example, housing 412 may be moved by one or two operators. In other advantageous embodiments, housing 412 may be located on a platform, such as a truck or a trailer that may be moved with respect to structure 404. Detector 410 detects collimated x-ray beam 414, which is emitted by x-ray source 408.

In these illustrative examples, detector 410 may take a number of different forms. For example, without limitation, detector 410 may be at least one of a scintillator, a semiconductor detector, a silicon drift detector, a film, and some other suitable type of detector.

Laser system 416 is configured to emit laser beam 424. Steering system 420 is configured to control the direction of laser beam 424. In this example, steering system 420 may comprise a number of mirrors that direct laser beam 424 within housing 412.

Portion 426 of laser beam 424 is directed by steering system 420 into gas source 418. In these examples, gas source 418 may be, for example, without limitation, a gas jet, gas in a capillary tube, or some other source of gas. The interaction between laser beam 424 and gas source 418 generates electron beam 428. In the illustrative examples, any gas capable of causing electron beam 428 to be generated when laser beam 424 hits gas source 418 may be used. For example, the gas in gas source 418 may be helium.

Further, steering system 420 directs portion 430 of laser beam 424 into electron beam 428 at focal point 432. In the illustrative examples, steering system 420 may be implemented using mirrors. Some of the mirrors may be partially reflective, while other mirrors may be fully reflective.

The interaction between electron beam 428 and portion 430 of laser beam 424 results in collimated x-ray beam 414. In these examples, collimated x-ray beam 414 is a beam with rays that are substantially or nearly parallel. Thus, collimated x-ray beam 414 spreads more slowly as collimated x-ray beam 414 propagates as compared to a non-collimated x-ray beam.

In the illustrative examples, x-ray source 408 and detector 410 are positioned relative to structure 404 to make measurements 402 for number of features 434 at location 436 on structure 404. Number of features 434 may include at least one of a gap, an edge, a fit up, and/or some other suitable feature at location 436. In these illustrative examples, x-ray source 408, detector 410, and structure 404 are positioned relative to each other to perform tangent radiography. In other words, collimated x-ray beam 414 is emitted from x-ray source 408, such that collimated x-ray beam 414 passes through number of features 434 tangentially on structure 404 to reach detector 410.

X-ray source 408 may include a laser wakefield accelerator in these illustrative examples. The laser wakefield accelerator may allow x-ray source 408 to emit collimated x-ray beam 414 at a substantially single energy level. This substantially single energy level may be equal to or greater than around one megavolt.

Controller 422 controls the operation of laser system 416 in these examples. Controller 422 is configured to control the emission of laser beam 424 from laser system 416. For example, controller 422 may control wavelength 440 of laser beam 424. Wavelength 440, in these illustrative examples, may vary, depending on the particular implementation. For example, without limitation, wavelength 440 may be from around 300 nanometers to around 1200 nanometers.

In these illustrative examples, detector 410 may be connected to computer 442, which includes processor unit 444 and number of storage devices 446. Computer 442 may receive information 448 from detector 410. Information 448 may be stored on number of storage devices 446. Further, processor unit 444 in computer 442 may execute program 450. Program 450, in these examples, may display image 452 on display device 454 using information 448. Additionally, program 450 also may use information 448 to generate measurements 402 for analysis. In this manner, the different advantageous embodiments may be used to generate measurements 402 for number of features 434 on structure 404.

The illustration of measurement environment 400 is not meant to imply physical or architectural limitations to the manner in which different advantageous embodiments may be implemented. Other components in addition to and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

For example, in some advantageous embodiments, processor unit 444, number of storage devices 446, and display device 454 may be located in housing 412. In yet other advantageous embodiments, computer 442 may be in a location remote to measurement environment 400. In still other advantageous embodiments, laser system 416 may include two laser sources instead of one laser source.

In other advantageous embodiments, additional detectors, in addition to detector 410, may be present. With this type of implementation, the additional detectors are placed in locations for other features in other locations on structure 404. X-ray source 408 may be moved or rotated to make measurements of the other number of features without repositioning the detectors. In other advantageous embodiments, detector 410 may not be connected to computer 442. For example, when detector 410 is a film, detector 410 is not connected to computer 442.

The different advantageous embodiments take into account and recognize that the different advantageous embodiments may allow an x-ray source to emit directional collimated x-ray beams at different substantially single energy levels for different types of measurements faster than currently available x-ray sources. In other words, x-ray source 408 may be capable of being controlled to emit different directional collimated x-ray beams at different substantially single energy levels with reduced times for operating x-ray source 408 as compared to currently available systems.

Figure 5:
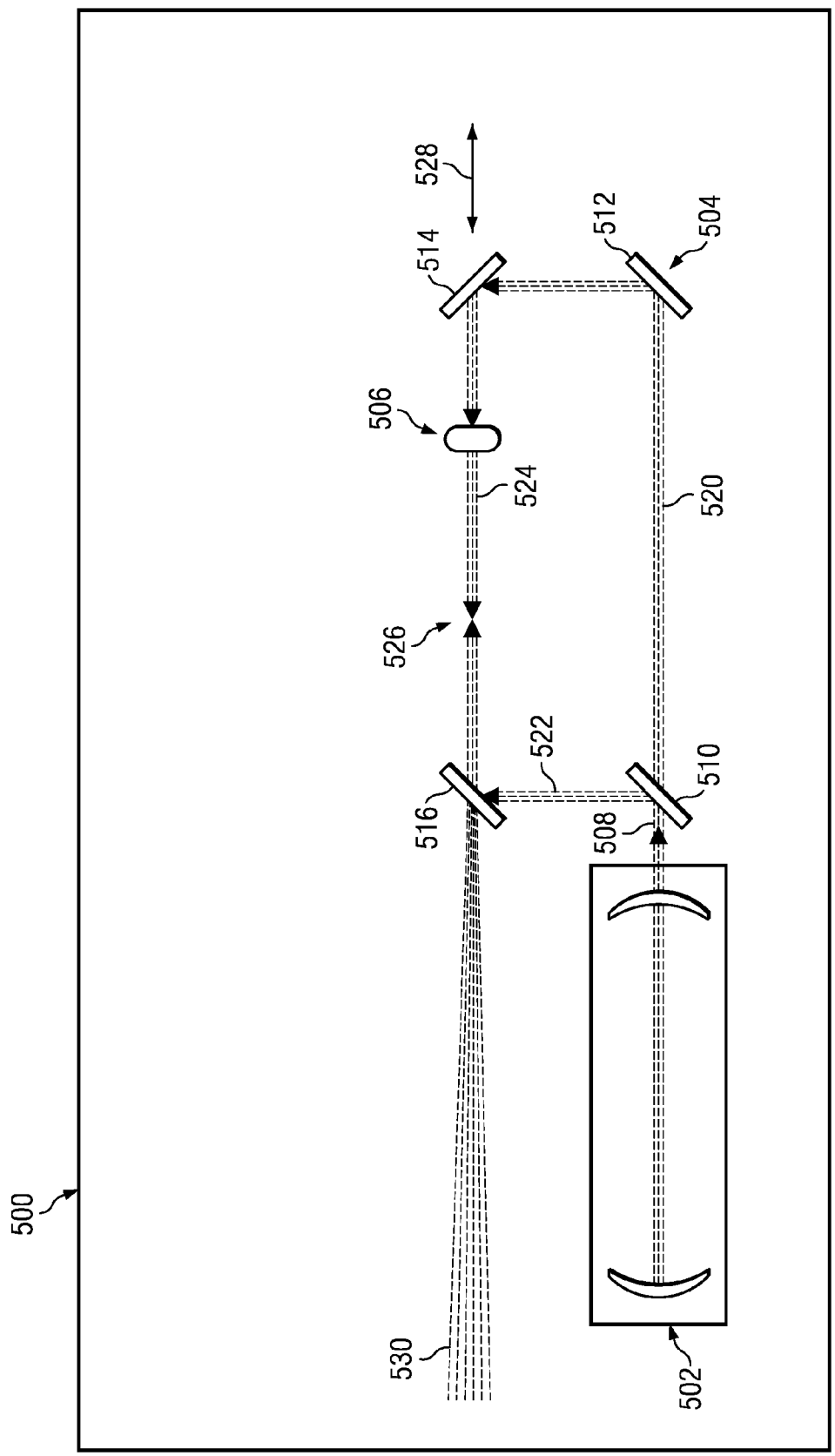
FIG. 5 is an illustration of a laser source in accordance with an advantageous embodiment.

With reference now to FIG. 5, an illustration of an x-ray source is depicted in accordance with an advantageous embodiment. X-ray source 500 is an example of one implementation for x-ray source 408 in FIG. 4. In this illustrative example, x-ray source 500 includes a laser wakefield accelerator to generate an electron beam. The electron beam interacts with a laser beam to generate a collimated x-ray beam.

In this illustrative example, x-ray source 500 includes laser 502, steering system 504, and gas source 506. As illustrated, laser 502 emits laser beam 508. Steering system 504 includes mirrors 510, 512, 514, and 516. Mirror 510 is partially reflective. In other words, portion 520 of laser beam 508 passes through mirror 510, while portion 522 is reflected by mirror 510 to mirror 516.

Steering system 504 causes portion 520 of laser beam 508 to pass through gas source 506. The interaction between gas source 506 and portion 520 of laser beam 508 results in electron beam 524. Steering system 504 causes portion 522 of laser beam 508 to intersect and/or interact with electron beam 524 at focal point 526. In this illustrative example, portion 522 of laser beam 508 encounters electron beam 524 along axis 528. In other words, portion 522 of laser beam 508 may be substantially collinear to electron beam 524 when portion 522 and electron beam 524 encounter each other at focal point 526. The point at which portion 522 of laser beam 508 and electron beam 524 encounter each other is substantially the point where collimated x-ray beam 530 is emitted.

Figures 6, 7:
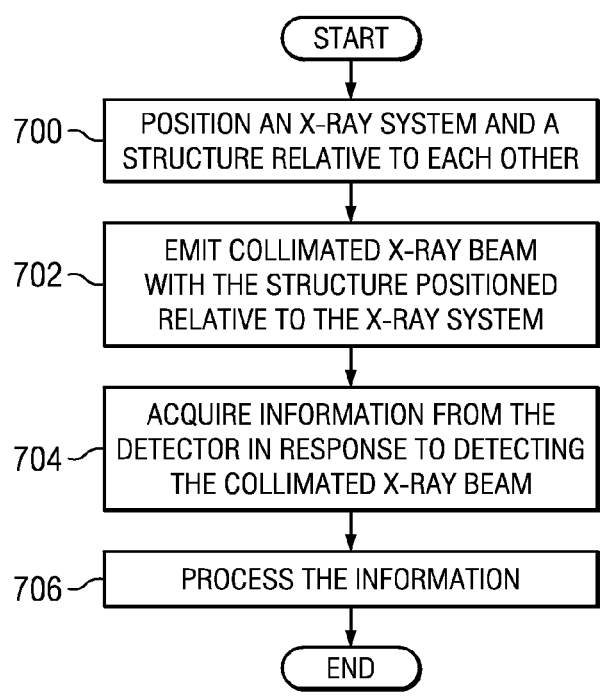
FIG. 6 is an illustration of a table comparing a currently used x-ray source with an x-ray source in accordance with an advantageous embodiment.
FIG. 7 is an illustration of a flowchart of a process for measuring a structure in accordance with an advantageous embodiment.

With reference now to FIG. 6, an illustration of a table comparing a currently used x-ray source with an x-ray source is depicted in accordance with an advantageous embodiment. In this illustrative example, table 600 compares the performance of an x-ray source using a linear accelerator, which is a currently used x-ray source, and an x-ray source using a laser wakefield accelerator. In this illustrative example, table 600 has columns 601, 602, and 604 and rows 606, 608, 610, 612, 614, and 616.

Column 601 represents the performance criteria for the comparison of the linear accelerator and the laser wakefield accelerator. Column 602 represents an x-ray source using the linear accelerator. Column 604 represents an x-ray source using the laser wakefield accelerator.

As depicted in row 606 of table 600, the laser wakefield accelerator has a focal spot size smaller than the linear accelerator. As depicted in row 608, the laser wakefield accelerator provides reduced image unsharpness as compared to the linear accelerator. Further, as depicted in rows 610 and 612, the laser wakefield accelerator has an x-ray beam and an electron beam with higher energy levels than the linear accelerator.

Still further, the x-ray source using the laser wakefield accelerator has a smaller cone angle in degrees than the linear accelerator, as depicted in row 614. The cone angle is the angular pattern with which the x-ray beam is emitted. The smaller cone angle allows a collimated x-ray beam to be emitted. Row 616 represents the x-ray flux in relation to the distance between the x-ray source and a detector. The laser wakefield accelerator x-ray source has an x-ray flux level that decreases with an increased x-ray source-to-detector distance at a rate slower than the linear accelerator x-ray source.

Turning now to FIG. 7, an illustration of a flowchart of a process for measuring a structure is depicted in accordance with an advantageous embodiment. In this illustrative example, the process illustrated in FIG. 7 may be implemented in measurement environment 400 in FIG. 4. In particular, the measurements may be made using x-ray system 406 in FIG. 4.

The process begins by positioning an x-ray system and a structure relative to each other (operation 700). In this example, the x-ray structure comprises a gas source, a laser system, and a detector. The gas source is configured to provide a gas, and the laser system is configured to emit a laser beam. The steering system is configured to direct a first portion of the laser beam into the gas, such that an electron beam is generated by the laser beam interacting with the gas. The steering system is also configured to direct a second portion of the laser beam into the electron beam, such that a collimated x-ray beam is formed. The detector is configured to detect the collimated x-ray beam.

The process emits the collimated x-ray beam with the structure positioned relative to the x-ray system (operation 702). In these examples, the collimated x-ray beam is emitted substantially tangential to a feature on the structure with the structure positioned relative to the x-ray system. Information is acquired from the detector in response to detecting the collimated x-ray beam (operation 704).

The information is then processed (operation 706), with the process terminating thereafter. The processing of the information may include generating an image from the information, presenting measurements, performing a test using the information, and/or other suitable operations.

Figure 8:
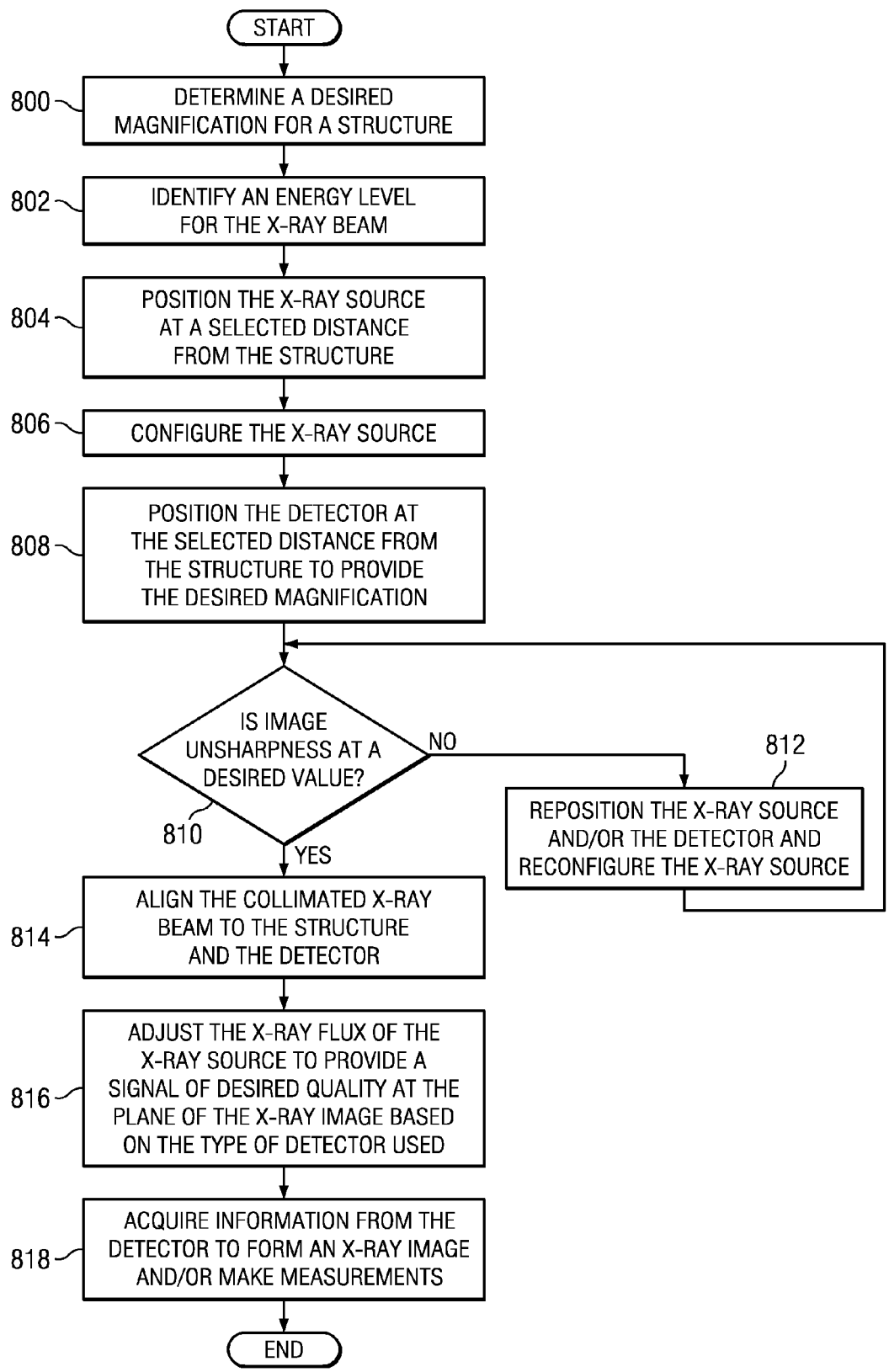
FIG. 8 is an illustration of a flowchart of a process for configuring an x-ray system in accordance with an advantageous embodiment.

With reference now to FIG. 8, an illustration of a flowchart of a process for configuring an x-ray system is depicted in accordance with an advantageous embodiment. The process illustrated in FIG. 8 may be implemented using an x-ray system, such as x-ray system 406 in measurement environment 400 in FIG. 4. The process may be used to obtain information for making measurements and/or performing an analysis of a structure.

The process begins by determining a desired magnification for a structure (operation 800). The desired magnification may be determined based on a number of factors such as, for example, a selected distance between the structure and the detector, a desired spatial resolution, and/or some other suitable factor. The distance between the structure and the detector may be selected based on the size and/or shape of the structure. In other words, the size and/or shape of the structure may result in the detector being positioned more than a desired distance from the structure.

In some illustrative examples, the distance between the structure and the detector may be selected based on the desired magnification. For example, as the desired magnification increases, the distance between the structure and the detector may be increased. Further, as the distance between the structure and the detector is increased, the magnification increases. The magnification and the distance between the structure and the detector may be related by the following equation:

$$M=(OD+SO)/SO,$$

wherein M is the magnification, OD is the distance between the structure and the detector, and SO is the distance between the x-ray source and the structure.

The desired magnification also may be selected based on a desired spatial resolution. The desired spatial resolution may be selected such that the x-ray information can be viewed as an image and/or analyzed to identify a number of features of interest. The size at which a number of features can be identified may vary depending on the spatial resolution. In other words, as the spatial resolution increases, the size of the number of features of interest that may be detected decreases.

The process then identifies an energy level for the x-ray beam (operation 802). The energy level for an x-ray beam to penetrate a structure varies with the thickness of the structure. For example, as the thickness of a structure increases, the level of energy that allows the x-ray beam to penetrate the thickness of the structure also increases.

Thereafter, the process positions the x-ray source at a selected distance from the structure (operation 804). This distance may be selected using the desired magnification identified in operation 800.

The process then configures the x-ray source (operation 806). The x-ray source is configured to provide a selected focal spot size and an x-ray beam with the energy level as determined in operation 802. The focal spot may have a substantially circular, substantially square, and/or some other suitable type of shape. The size of the focal spot is measured as the diameter or width of the focal spot.

The process then positions the detector at the selected distance from the structure to provide the desired magnification (operation 808). Thereafter, the process determines whether image unsharpness is at a desired value (operation 810). Image unsharpness is the blurring of the edge of a structure in the x-ray image. The blurring that occurs may be based on geometric properties of the x-ray system and the structure. For example, these geometric properties include, without limitation, the focal spot size and the distance between the x-ray source and the structure.

The desired value for image unsharpness is a size less than the desired spatial resolution in these illustrative examples. Image unsharpness may be related to the magnification and focal spot size by the following equation:

$$U=f(M-1),$$

wherein U is unsharpness, f is the focal spot size, and M is the magnification. If the image unsharpness is not at the desired value, the process may reposition the x-ray source and/or detector and may reconfigure the x-ray source (operation 812). The process may then return to operation 810).

If the image unsharpness is at a desired value, the process aligns the collimated x-ray beam to the structure and the detector (operation 814). Then, the process adjusts the x-ray flux of the x-ray source to provide a signal of desired quality at the plane of the x-ray image based on the type of detector used (operation 816).

The process acquires information from the detector to form an x-ray image and/or make measurements (operation 818), with the process terminating thereafter. The information may be presented as an image on a display device or printed on a medium for analysis and to make measurements. The information also may be used to make measurements without displaying an image on the display device. These measurements and/or analysis of images may be part of a nondestructive test of the structure.

The flowcharts and block diagrams in the different depicted embodiments illustrate the architecture, functionality, and operation of some possible implementations of apparatus and methods in different advantageous embodiments. In this regard, each block in the flowcharts or block diagrams may represent a module, segment, function, and/or a portion of an operation or step. In some alternative implementations, the function or functions noted in the blocks may occur out of the order noted in the figures. For example, in some cases, two blocks shown in succession may be executed substantially concurrently, or the blocks may sometimes be executed in the reverse order, depending upon the functionality involved.

Thus, the different advantageous embodiments provide a method and apparatus for measuring a structure. In the different advantageous embodiments, an x-ray system and a structure are in a position relative to each other. The x-ray system emits a collimated x-ray beam with the structure positioned relative to the x-ray system. The x-ray system includes an x-ray source and a detector. The x-ray source emits the collimated x-ray beam. The detector detects the collimated x-ray beam to generate information for the measurements.

With one or more of the different advantageous embodiments, a focal spot with a size capable of providing the desired levels of x-ray flux is present. Further, one or more of the different advantageous embodiments emits a collimated x-ray beam. This collimated x-ray beam may reduce the exposure to x-rays outside of a location in which a feature is present. Further, the different advantageous embodiments provide a capability to use an amount of energy that is capable of penetrating structures, such as an aircraft. Additionally, the different advantageous embodiments may include a portable x-ray system, which may be positioned around the aircraft rather than requiring the aircraft to be moved to the x-ray system.

The description of the different advantageous embodiments has been presented for purposes of illustration and description, and it is not intended to be exhaustive or limited to the embodiments in the form disclosed. Many modifications and variations will be apparent to those of ordinary skill in the art. Further, different advantageous embodiments may provide different advantages as compared to other advantageous embodiments.

Although the different advantageous embodiments have been described with respect to aircraft, the different advantageous embodiments also recognize that some advantageous embodiments may be applied to other types of platforms. For example, without limitation, other advantageous embodiments may be applied to a mobile platform, a stationary platform, a land-based structure, an aquatic-based structure, a space-based structure and/or some other suitable object. More specifically, the different advantageous embodiments may be applied to, for example, without limitation, a submarine, a bus, a personnel carrier, a tank, a train, an automobile, a spacecraft, a space station, a satellite, a rocket, a missile, a surface ship, a power plant, a dam, a manufacturing facility, a building, an engine, a frame, a wing, and/or some other suitable object.

The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for sending x-rays through a structure, the method comprising:
    positioning an x-ray system and the structure relative to each other, wherein the x-ray system comprises a gas source configured to provide a gas; a laser system configured to emit a laser beam; a steering system configured to direct a first portion of the laser beam into the gas such that an electron beam is generated by the laser beam interacting with the gas and configured to direct a second portion of the laser beam into the electron beam such that a collimated x-ray beam is formed; and a detector configured to detect the collimated x-ray beam;
    calculating a magnification by adding a first distance between the structure and the detector to a second distance between an x-ray source and the structure to get a sum and dividing the sum by the second distance;
    calculating an image unsharpness by multiplying a focal spot size by the magnification; and
    emitting the collimated x-ray beam substantially tangential to a location of a feature on the structure so that the collimated x-ray beam passes tangentially through the feature on the structure to reach a detector to produce an image with the image unsharpness.

2. The method of claim 1, wherein the gas source and the laser system are located in a housing and wherein the step of positioning the x-ray system and the structure relative to each other comprises:
    identifying the feature for the structure; and
    placing the housing in a first position based on the feature.

3. The method of claim 1 further comprising:
    identifying a desired magnification based on at least one of a distance between the structure and the detector and a desired resolution.

4. The method of claim 3, wherein the gas source and the laser system are located in a housing and wherein the step of positioning the x-ray system and the structure relative to each other comprises:
    placing the housing at the second distance.

5. The method of claim 4 further comprising:
    setting a substantially single energy level for the collimated x-ray beam.

6. The method of claim 1 further comprising:
    identifying an energy level for the collimated x-ray beam based on a thickness of the structure.

7. The method of claim 1 further comprising:
    obtaining information from the detector in response to emitting the collimated x-ray beam.

8. The method of claim 7 further comprising:
    processing the information to obtain at least one of an image and a number of measurements.

9. The method of claim 1, wherein the detector comprises at least one of a scintillator, a semiconductor detector, a silicon drift detector, an image intensifier, and a film.

10. The method of claim 1, wherein the laser beam has a wavelength from about 300 nanometers to about 1200 nanometers.

11. The method of claim 1, wherein the structure is selected from one of a mobile platform, a stationary platform, a land-based structure, an aquatic-based structure, a space-based structure, an aircraft, a surface ship, a tank, a personnel carrier, a train, a spacecraft, a space station, a satellite, a rocket, a missile, a submarine, an automobile, a power plant, a bridge, a dam, a manufacturing facility, an engine, a frame, a wing, and a building.

12. A method for sending x-rays through a structure, the method comprising:
    positioning an x-ray source and a detector relative to a feature in a location on the structure, wherein the x-ray source emits a collimated x-ray beam at a substantially single energy level, wherein the substantially single energy level is selected to allow the collimated x-ray beam to penetrate the structure, and wherein the x-ray source has a focal spot having a size selected for a desired magnification, a desired x-ray flux level, and a desired level of unsharpness;
    calculating a magnification by adding a first distance between the structure and the detector to a second distance between the x-ray source and the structure to get a sum and dividing the sum by the second distance;
    calculating an image unsharpness by multiplying a focal spot size by the magnification; and
    emitting the collimated x-ray beam from the x-ray source substantially tangential to a location of a feature on the structure with the structure positioned relative to the x-ray source so that the collimated x-ray beam passes tangentially through the feature on the structure to reach the detector to produce an image with the image unsharpness.

13. An apparatus comprising:
a gas source configured to provide a gas;
a laser system configured to emit a laser beam;
a steering system configured to direct a first portion of the laser beam into the gas such that an electron beam is generated by the laser beam interacting with the gas and configured to direct a second portion of the laser beam into the electron beam such that a collimated x-ray beam is formed;
a detector configured to detect the collimated x-ray beam; and
a computer configured to calculate a magnification by adding a first distance between the structure and the detector to a second distance between an x-ray source and the structure to get a sum and dividing the sum by the second distance, and configured to calculate an image unsharpness by multiplying a focal spot size by the magnification;
wherein the collimated x-ray beam is emitted substantially tangential to a location of a feature on a structure with the structure positioned relative to the steering system so that the collimated x-ray beam passes tangentially through the feature on the structure to reach the detector to produce an image with the image unsharpness.

14. The apparatus of claim 13 further comprising:
a processor unit configured to control the laser system to generate the laser beam.

15. The apparatus of claim 14, wherein the processor unit is configured to control a wavelength of the laser beam.

16. The apparatus of claim 15, wherein the wavelength is from about 300 nanometers to about 1200 nanometers.

17. The apparatus of claim 13 further comprising:
a portable housing, wherein the gas source, the laser system, and the steering system are located in the portable housing.

18. The apparatus of claim 13, wherein the detector comprises at least one of a scintillator, a semiconductor detector, a silicon drift detector, an image intensifier, and a film.

19. The apparatus of claim 13, wherein the collimated x-ray beam has a substantially single energy level.

* * * * *